US010376417B2

(12) United States Patent
Cumming et al.

(10) Patent No.: US 10,376,417 B2
(45) Date of Patent: *Aug. 13, 2019

(54) HEAD TRAUMA BANDAGE CAP AND METHOD

(71) Applicant: First Responder Solutions, LLC, Carmel, CA (US)

(72) Inventors: Michelle Cumming, Carmel, CA (US); Mitchell Kastros, Carmel, CA (US); Marc Etchells, Westhampton, MA (US); Paul E Lentz, III, Manchester, NH (US)

(73) Assignee: First Responder Solutions, LLC, Carmel, CA (US)

( * ) Notice: Subject to any disclaimer, the term of this patent is extended or adjusted under 35 U.S.C. 154(b) by 454 days.

This patent is subject to a terminal disclaimer.

(21) Appl. No.: 14/789,569

(22) Filed: Jul. 1, 2015

(65) Prior Publication Data

US 2017/0000651 A1    Jan. 5, 2017
US 2019/0209381 A9    Jul. 11, 2019

Related U.S. Application Data

(63) Continuation-in-part of application No. 13/560,410, filed on Jul. 27, 2012, now Pat. No. 9,149,393, which is a continuation-in-part of application No. 12/807,288, filed on Sep. 1, 2010, now Pat. No. 8,262,601.

(51) Int. Cl.
*A61F 13/00*    (2006.01)
*A61F 13/02*    (2006.01)
*A61F 13/12*    (2006.01)

(52) U.S. Cl.
CPC .. *A61F 13/00038* (2013.01); *A61F 13/00017* (2013.01); *A61F 13/00029* (2013.01);
(Continued)

(58) Field of Classification Search
CPC .. A42C 5/04; A42C 99/00; A42B 1/04; A42B 1/00; A42B 1/006; A42B 1/008; A42B 1/046; A42B 1/066; A42B 1/041; A42B 1/043; A42B 1/045; A42B 1/06; A42B 1/068; A42B 1/22; A42B 1/225; A42B 7/00; A42B 1/18; A61F 13/00038; A61F 13/00004; A61F 13/00017; A61F 13/00029; A61F 13/00046; A61F 13/00051; A61F 13/00008; A61F 13/00034; A61F 13/00042; A61F 13/00059; A61F 13/00063; A61F 13/12; A61F 13/122; A61F 13/00;
(Continued)

(56) References Cited

U.S. PATENT DOCUMENTS

| 945,839 A | 1/1910 | Brisbane |
|---|---|---|
| D295,446 S | 4/1988 | Lundell et al. |

(Continued)

*Primary Examiner* — Victoria J Hicks
(74) *Attorney, Agent, or Firm* — Marcus G. Theodore

(57) ABSTRACT

An emergency head trauma bandage cap with a detachable strap system and method of use, which, when applied to the head, delivers minimal pressure to control bleeding, doesn't compromise cervical spine immobilization, allows for fast and effective application of cooling gel to control intracranial/internal swelling or hot packs to prevent hypothermia in non-trauma situations, doesn't come apart during treatment and transport, and doesn't require a caregiver to re-wrap the dressing.

26 Claims, 14 Drawing Sheets

(52) U.S. Cl.
CPC .. *A61F 13/00042* (2013.01); *A61F 13/00046* (2013.01); *A61F 13/00051* (2013.01); *A61F 13/0286* (2013.01); *A61F 13/12* (2013.01)

(58) Field of Classification Search
CPC ............... A61F 13/45; A61F 13/15; A61F 2013/15008; A61F 2013/00089; A61F 2013/00187; A61F 2013/00246; A61F 5/00; A61F 7/00; A61F 2007/001; A61F 2007/0002; A61F 2007/0007; A61F 2007/0008

See application file for complete search history.

(56) References Cited

U.S. PATENT DOCUMENTS

| | | |
|---|---|---|
| 4,744,106 A | 5/1988 | Wang |
| 5,031,609 A | 7/1991 | Fye |
| 5,044,031 A | 9/1991 | Sherwood |
| 5,173,970 A | 12/1992 | Shifrin |
| 5,305,470 A | 4/1994 | McKay |
| D354,376 S | 1/1995 | Kun |
| 5,557,807 A | 9/1996 | Hujar et al. |
| 5,666,668 A | 9/1997 | Ronquillo |
| 5,860,292 A | 1/1999 | Augustine et al. |
| 5,960,477 A | 10/1999 | Dixon |
| 6,228,041 B1 | 5/2001 | Ameer |
| 6,678,896 B2 | 1/2004 | Robinson et al. |
| 6,747,561 B1 | 6/2004 | Reeves |
| 6,762,337 B2 | 7/2004 | Boukanov et al. |
| 7,744,640 B1* | 6/2010 | Faries, Jr. ............... A61F 7/007 607/109 |
| 9,149,393 B2* | 10/2015 | Cumming ............... A61F 13/12 |
| 2005/0027227 A1 | 2/2005 | Dumas et al. |
| 2005/0193491 A1 | 9/2005 | Zucker et al. |
| 2007/0074326 A1 | 4/2007 | Komachak |
| 2012/0296252 A1* | 11/2012 | Cumming ............... A61F 13/12 602/45 |

\* cited by examiner

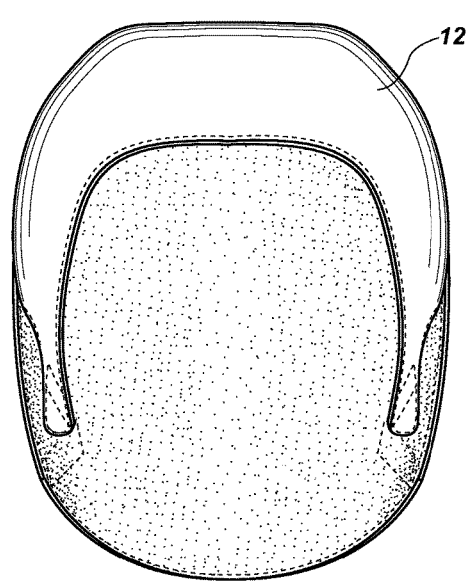
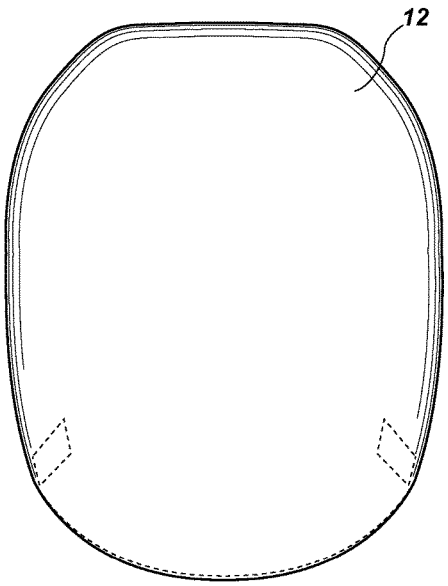
FIG. 3        FIG. 4
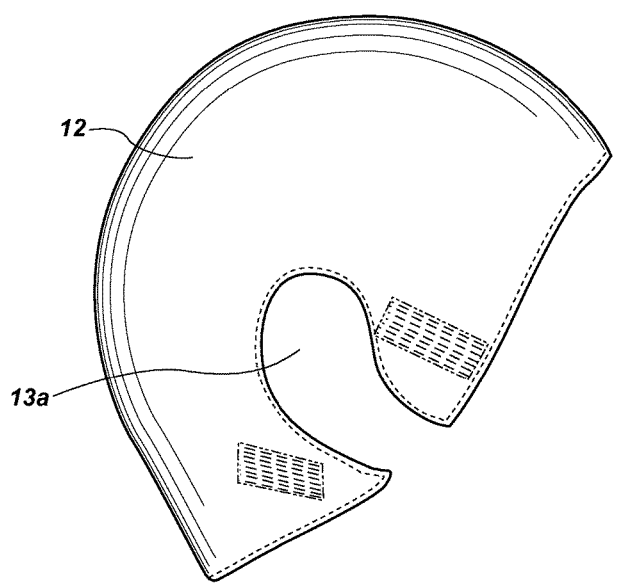
FIG. 5

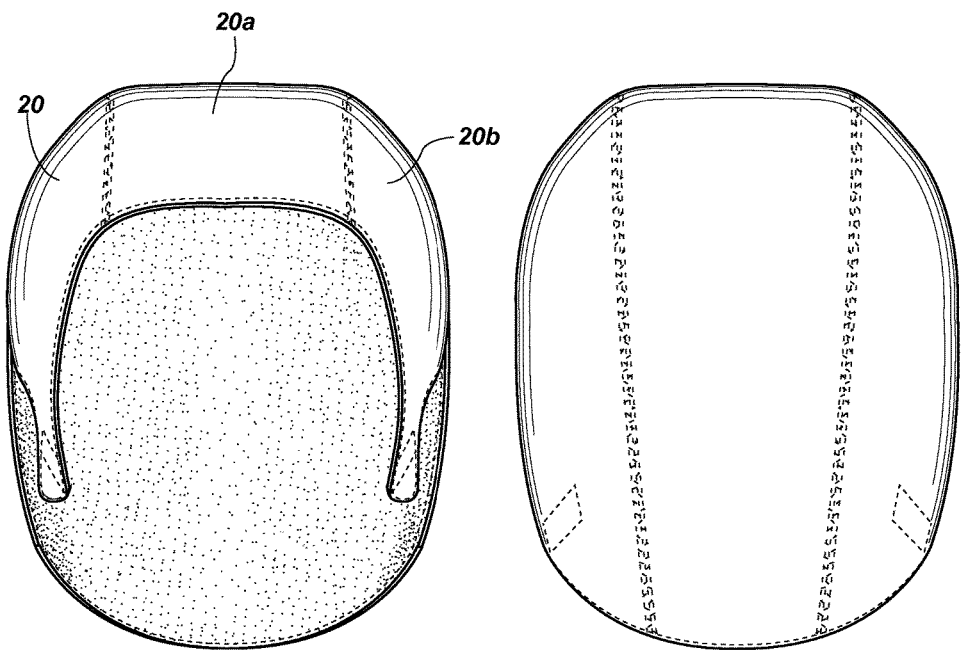
FIG. 10   FIG. 11
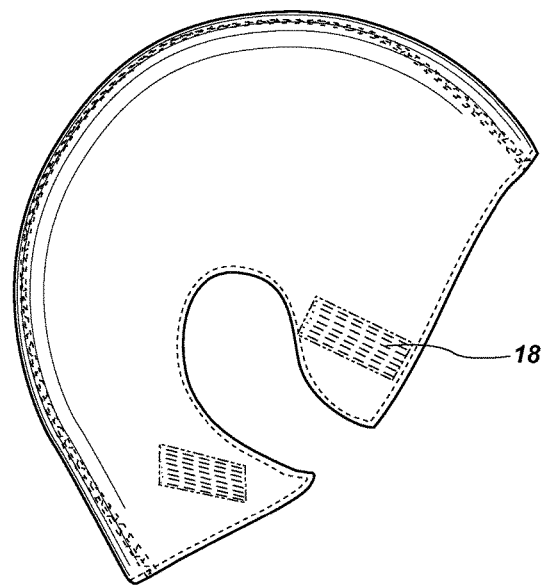
FIG. 12

HEAD TRAUMA BANDAGE CAP AND METHOD

RELATED APPLICATIONS

This application is a continuation-in-part patent application of the continuation-in-part patent application entitled "Head Trauma Bandage Cap and Method", Ser. No. 13/560,410, filed Jul. 27, 2012, which is a continuation-in-part patent application entitled "Helmet Trauma Bandage and Method", Ser. No. 12/807,288 filed Sep. 1, 2010.

BACKGROUND OF THE INVENTION

Field

The present invention relates to bandages and trauma treatment. In particular, it relates to a method of use and an emergency trauma bandage cap with or without pouches for hot or cold packs, which is placed on the cranium to cover the crown, forehead, back of the head, sides of the head around the ears, and the temples of an injured patient with minimal movement of the neck and spine.

Description of Related Art

Various bandages are known in the art. Boukanov et al., U.S. Pat. No. 6,762,337 issued Jul. 13, 2004 discloses a multi-purpose pressure bandage for body wounds utilizing an expansion bladder, which inflates to compress an affixed bandage against an injured patient's wounds. The Boukanov et al. specifically states its system design is to provide a pressure dressing. To apply pressure, the device incorporates the use of a carbon dioxide gas container with an inlet valve for inflating a bladder in the bandage on site to apply additional pressure (resistance pressure or inflating to create pressure) to the wound to control bleeding.

The Boukanov et al. embodiment for head wounds has the compression bandage shaped like a cap to secure about the head. The Boukanov et al head bandage configuration has a bladder with a coextensive gauze bandage liner and a gas cartridge hidden in a pouch at a bottom edge. Elongated straps extend diametrically from the bottom edge for securing the dome-shaped pressure bandage to a head injury. Once in place, the bladder of the bandage is inflated to apply pressure to the wound. Although the application of pressure to control bleeding is taught to be the standard when treating soft tissue injuries, it is contraindicated with regard to bleeding associated with a head injury, requiring only gentle pressure.

Boukanov et al.'s compression bandage is not suitable for head injuries. Head injuries are usually associated with intracranial swelling, which causes excess pressure on the brain and towards the skull. Pressure treatment similar to Boukanov et al. applied to a head injury through compression compounds the problem of internal pressure to the brain and skull. Through this compression method the pressure applied by treating the injury creates even more pressure on the brain, and this can lead to a rapid deterioration of the condition of the patient. In addition, long-term and permanent brain damage can occur from the application of a pressure dressing, which, in the worst case, can lead to the death of the patient.

The standard of treatment for a head injury is to apply gentle pressure for controlling bleeding, and for applying a cold pack to control intracranial swelling associated with head trauma. The idea of applying "gentle pressure" is to not exceed the amount of pressure being exerted inside the cranium resulting from head trauma. The present invention discussed below is designed to be consistent with the standard for treating head injuries, and does not have any similarities with the Boukanov et al bladder compression system with regard to its application. It does not have any features, which create excess pressure, compromise cervical-spinal precautions or in any other way challenge the well being of the patient with a head injury.

If the Boukanov et al. bladder pressure regulator fails, it also may result in significant pressure, which can cause serious head injuries where intra cranial fluids build up causing the head to swell. In addition, if improperly inflated, circulation may be cut off. The bandage also suffers from compression problems if the gas container is empty, or fails to inflate the bladder. Under these circumstances, the Boukanov et al pressure bandage may aggravate the patient's head injuries. Further, if the Boukanov et al. bladder is pierced accidentally during emergency use, an ill-fitting head wrap results.

Lundell et al., U.S. Pat. No. Des. 295,446, issued Apr. 26, 1988 is a head bandage protector that would require first conventionally wrapping the patent with bandages, which may compromise cervical spine immobilization depending upon how the bandage wraps are administered.

Fye, U.S. Pat. No. 5,031,609, issued Jul. 16, 1991 is a postoperative compression bandage for the head, which would also require conventional bandaging before compression application; again possibly compromising cervical spine immobilization.

Neither Lundell et al, nor Fye are bandages with a weather resistant cover for rapid application in the field to avoid moving the neck or spine during emergency trauma applications.

Cited for general interest are: Sherwood, U.S. Pat. No. 5,044,031, issued Sep. 3, 1991 discloses passive warming articles for traumatized individuals suffering from hypothermia, shock or exposure. Kun, U.S. Pat. No. Des. 354,376, issued Feb. 14, 1995 discloses a head-cooling cap. Hujar et al., U.S. Pat. No. 5,557,807 issued Sep. 24, 1996 discloses headwear including coolant means. Ameer, U.S. Pat. No. 6,228,041, issued May 8, 2001 discloses a lightweight portable scalp vibrating and hair growth-stimulating device. Komacha; U.S. Publication No. US2007/0074326, dated Apr. 5, 2007, discloses a headgear with cooling device formed using a woven or non-woven material. Wang, U.S. Pat. No. 4,744,106, issued May 17, 1988 discloses an engineering cap with fan device structure for ventilation of the hard hat. Augustine et al., U.S. Pat. No. 5,860,292 issued Jan. 19, 1999 discloses an inflatable thermal blanket with head covering for convectively cooling the body. Robinson et al., U.S. Pat. No. 6,678,896, issued Jan. 20, 2004 discloses a sports towel. Ronquillo, U.S. Pat. No. 5,666,668 issued Sep. 16, 1997 discloses a cap with front size adjustment and rear flap. Dixon, U.S. Pat. No. 5,960,477 issued Oct. 5, 1999 discloses a hat with folded rim and visor. Dumas et al., U.S. Pub. No. 2005/0027227 published Feb. 3, 2005 discloses a disposable water resistant cover for medical applications. Reeves, U.S. Pat. No. 6,747,561 issued Jun. 8, 2004 discloses a bodily worn device, which provides for digital storage and retrieval of a user's medical records, drug prescriptions, medical history, organ donor instructions, and personal identification for use in an emergency or routine medical situation. Zucker et al., U.S. Publication No. US2005/0193491 published Sep. 8, 2005, discloses a pediatric emergency transport device. McKay, U.S. Pat. No. 5,305,470, issued Apr. 26, 1994 discloses a sports band.

Brisbane, U.S. Pat. No. 945,839, issued Jan. 11, 1910 is a sleeping cap unsuitable for use as a bandage, and may not expand sufficiently to accommodate larger heads. The elasticized Brisbane sleeping cap using elasticized side to apply pressure for holding the cap onto the head could adversely affect intracranial pressure from a head wound and aggravate the wound tissue when slid over the head. Dixon, U.S. Pat. No. 5,960,477, issued Oct. 5, 1999, is a snow hat with folded rim requiring the head to be lifted for placement, again aggravating spinal injuries. Dumas et al. U.S. Publication 2005/0027227 published Dec. 3, 2005 is a medical disposable water resistant cover for medical applications. Shfifin, U.S. Pat. No. 5,173,970, issued Dec. 29, 1992 discloses a visored cap-type protective segmented helmet for bicyclists and the like, which can be used as a pouch.

None of the above references provides an emergency head bandage, which doesn't compromise cervical spine immobilization when applied, doesn't come apart during treatment and transport, and doesn't require a caregiver to re-wrap the dressing. The improved invention discussed below can be quickly applied as a bandage dressing to control bleeding and/or a device to hold cold packs in place to gently control intracranial pressure. These features can be used separately or in conjunction with a single application of the cap, depending on the medical needs of the patient with regard to head trauma. The invention described below provides such an invention and method of using it.

SUMMARY OF THE INVENTION

The present invention comprises a trauma bandage cap and method. It is structured as a flexible cap with periphery edges, segments, and an opening sized to fit about and cover the forehead/crown, sides, and back of the head of a patient with a head trauma. The cap segments proximate the ears define ear observation cutouts to reveal any fluid discharge from the ears.

The cap is constructed of absorbent, medical-grade materials that have a non-adherent layer positioned directly in contact with the head or skin. The cap is made of materials with enough flexibility when placed on a patient and strapped with a chinstrap to apply minimal pressure to the head to control bleeding without aggravating intracranial pressure.

Exterior pouches may or may not be affixed to the exterior of the flexible cap and structured to removably receive and secure therein hot or cold packs. The type of pack is selected depending upon whether cold applications are required to stop further swelling, or whether hot applications are required to help prevent hypothermia in non-head trauma situations.

Alternatively, on demand cool-packs may be employed into the flexible trauma bandage cap. The on-demand cool feature requires a Two-Part chemistry. One is a solid that would be incorporated into an interior layer and the second is a liquid reservoir, pouch or ampule. This reservoir is broken to release the fluid, which starts an endothermic reaction, cool. The reservoir would be activated prior to placing the Trauma bandage cap on the patient, or could be activated when in-use. Multiple zones could be designed, left/right or front/back for example. The cooling effect is temporary (15-min or so) and the product remains single-use.

In one embodiment, there are four exterior pouches positioned to cover respectively the forehead/crown, back and sides of the head. Each pouch is structured with top openings leading into interiors into which hot or cold packs are inserted and secured therein with openable fasteners before subsequent removal. A detachable strap system is releaseably affixed to the cap periphery edges and structured to fit securely across a patient's chin to hold the cap in place in a manner which applies minimal pressure to control bleeding, but can also be loosened and re-attached to prevent circulation restriction and avoid aggravating intracranial pressure.

The periphery segments of the cap are cut in such a way to expose the ears with openings on both sides of the cap to allow for observation of the ear canals. In one embodiment, a removable chinstrap affixed with hook and loop strips fits across the chin of the patient and is secured to the cap on either side of the ear openings. This allows the chinstrap to be properly secured to the patient from both sides. Further, the chinstrap may be affixed in a manner so that the opening of the observation holes may be varied in size as the strap fastener is varied in position.

Preferred fasteners are hook and loop strips, but other fasteners, such as snaps, hooks, buttons, etc. could be used to secure the strap ends. However, these are more complicated to use in the field, and are more expensive and difficult to adjust.

One embodiment of this cap includes an impermeable film which forms the outer layer, and an inner layer formed of a suitable soft textile or nonwoven material. On one side of this nonwoven material an apertured net known as a "non-adherent wound contact layer" would be affixed in some manner, preferably laminated, to the inside surface which would be in contact with the patient's wound.

The impermeable film, which forms the outer layer may include layers of film and reinforcing and/or cushioning materials, which together form a composite structure. Film offers the advantage of providing a barrier toward the penetration of bacteria, pathogens or contaminants. The ideal product is a monolithic barrier film, which allows air permeability but resists fluid penetration. When such a layer is placed over the skin, moisture or perspiration from the skin can escape. This type of waterproof-breathable film is also a bacterial and viral barrier and there are no holes or direct passages thru the monolithic film layer. Moisture passes thru the molecular structure, which is hydrophilic and moisture-permeable. Polyurethanes, polyolefins, polyesters (such as DuPont's Hytrel®), block-copolymers, and blends, are generally used in such waterproof-breathable films. A "barrier-dressing" feature results as exterior particles, fluids and pathogens cannot penetrate from the outside toward the patient.

The cap thus is a composite structure with conformability. The basic material composite construction remains the same, but the thickness has been reduced for added conformability. This requires a careful optimization of process conditions to allow the attachment of the waterproof breathable outer urethane to the low melt-point wound contact surface. Thickness is reduced and flexibility is increased. A better trauma bandage cap results. Typical thicknesses and stiffness criteria are shown in the table below:

|  | Individual Raw Material Thickness | | | |
| --- | --- | --- | --- | --- |
|  | Original inches* | Improved inches* | Improved with absorbent - Dry inches* | Improved with absorbent - Wet** inches* |
| Film | 0.004 | 0.004 | 0.004 | 0.04 |
| Nonwoven 1 | 0.074 | | | |

-continued

| | Individual Raw Material Thickness | | | |
|---|---|---|---|---|
| | Original inches* | Improved inches* | Improved with absorbent - Dry inches* | Improved with absorbent - Wet** inches* |
| SAF absorbent layer | | | 0.018 | 0.064 |
| Nonwoven with Non-Adherent Layer | 0.032 | 0.032 | 0.032 | 0.032 |
| Thickness as a composite | 0.074 | 0.028 | 0.040 | 0.090 |

*Measured with an Ames Gauge, 10-oz load 1-inch diameter measurement area
**3-min exposure to 0.9% saline, same load as above In this same embodiment, the inside layers are formed of a suitable soft textile or nonwoven material. Traditional bleached cotton gauze is suitable for the interior wound-contact layer but there are other alternatives. Several nonwoven fabrics are suitable, especially hydro-entangled and needle-punched materials. The fiber blend can range from cotton or rayon to Lyocell (Lenzing's Tencel®) to polyester or polypropylene. Many blends are possible as are fibers of different diameters. Hydrophilic and or hydrophobic fibers or chemical treatments can be utilized. A preferred material is a polyester/rayon needle-punched blend in the weight range of 100 to 200 grams/square meter. On one side of this material is laminated an apertured net known as a "non-adherent wound-contact layer". The polyolefin polymer blend of this layer provides a hydrophilic surface that resists attachment to wounds while allowing fluids and moisture to easily pass thru the voids and into the needle-punch layer or other absorbent layer(s). This general structure is utilized in many finger bandages and 4"×4" pads for first aid use.

For fluid management, a thin nonwoven layer selected to provide additional blood holding capacity is employed similar to that used for panty-liners, baby diapers and new wound care dressings. This added structure (layer) is embedded in all or part of the composite cap structure. It utilizes the fibrous format of superabsorbent polymer (SAP) chemistry. The fiber SAP, often called Super Absorbent Fiber (SAF), is soft, flexible and eliminates possible contamination from granular formulations. The fibrous SAP layer can be hydrated and chilled or frozen to provide an extended duration cooling device that is already formed into the head shape for this specific application. Many physical therapy cool packs utilize a similar technology now. Those pads or shaped articles are reusable. A pre-chilled Trauma Beanie would be a single use item. Materials cost increases are minimal. The drawback is the requirement to pre-cool the device, making it particularly suitable for hospital use where cooling facilities are readily available.

Another possible material used in the construction of the cap, could be a cotton Spandex, Lycra or elastane synthetic fiber known for its exceptional elasticity. It is stronger and more durable than natural rubber. It is a polyester-polyurethane copolymer (such as Dupont's LYCRA®), a man-made elastane fiber. Never used alone, but always blended with other fibers, it has unique stretch and recovery properties. LYCRA® fiber adds comfort, fit, shape retention, durability and freedom of movement. This is achieved by the unique properties of the fiber, which can be stretch up to seven times its initial length before springing back to the original position once tension is released. Any natural or man-made fibers can be mixed with LYCRA® fiber. Very small amounts of LYCRA® fiber in a material can be as little as 2%. There are various ways of integrating LYCRA® fiber with other fibers to provide fabrics for all needs.

As many wounds have been exposed to dirt and pathogens, it may also be advantageous to utilize an infection-control strategy. In these embodiments, traditional silver-ion releasing antimicrobials may be used and are recognized as effective in reducing bacterial populations and thus infections. Antimicrobials more rapid than silver include stabilized Hydrogen Peroxide, quaternary amines and oxidizers like iodine, chlorine or chlorhexidine gluconate (CHG). The antimicrobial may be placed in the non-adherent net, the absorbent layer and/or in the waterproof-breathable outer layer. A preferred system is 200 ppm of elemental silver in the Polyurethane polymer blend of the "0.004" thick outer layer.

For some cap materials, preferred construction is with ultrasonic seaming and welding, as it does not use needles and thread, eliminating color changes, thread unraveling, and penetrations in the protective outer layer. Seam welding is particularly suited to secure inner gauze liners to the shell to prevent frayed ends. It is also useful to join the sections of the outer shell. These ultrasonic sewing machines, which function by high frequency vibrating and heating outer layers of material, which then fuse, are also suited for use in clean room production facilities.

However, where cotton fabrics are used, conventional sewing and stitching is employed using hook and loop strips, rivets, snaps, and adhesive tape. For other materials, ultrasonics, heat and pressure and hot melt methods of assembly may be employed. An alternative to ultrasonic welding is radio frequency or RF welding which welds via internal heating of the materials and layers, which fuse.

A permanently flexible adhesive may also be used for assembly. This is not tacky like a pressure sensitive adhesive (PSA), but is cured in-place with a UV cure adhesive that is flexible and differs from most UV cure adhesives, which are hard and brittle when cured with a high intensity traditional curing system emanating heat at or above the melt point of the urethane, causing holes and puckering. Instead, a low-power LED is used to generate the desired UV cure wavelength, which does not emit sufficient harmful heat to distort the finished product. UV exposure and cure is effectuated without the lengthy exposure time of older systems, which is now reduced to several seconds. The new UV cure offers almost immediate curing (crosslinking) of the flexible adhesive. In one embodiment, the cap may be color-coded and then placed on the patient to indicate the severity of a patient's injuries and/or the proper positioning of the cap on the patient. Color codes are also used to identify patients who have been given a medication or treatment, which requires special handling by emergency trauma teams. This is particularly important for field disasters requiring triage color categorization. In advanced triage systems, secondary triage is typically implemented by paramedics, emergency medical technicians, battlefield medical personnel or by skilled nurses in the emergency departments of hospitals, and during disasters where injured people are sorted into five categories (note; categories and color coordinates may vary according to regions and other requirements dictated by policy:

Black/Expectant (Monterey County, California category is "Morgue," Pulseless/Non-Breathing)

They are so severely injured that they will die of their injuries, possibly in hours or days (large-body burns, severe trauma, lethal radiation dose), or in life-threatening medical crisis that they are unlikely to survive given the care available (cardiac arrest, septic shock, severe head or chest wounds); they should be taken to a holding area and given painkillers as required to reduce suffering.

Red/Immediate (same in Monterey County, Calif.)

They require immediate surgery or other life-saving intervention, and have first priority for surgical teams or transport to advanced facilities; they "cannot wait" but are likely to survive with immediate treatment.

Yellow/Observation (Monterey, Calif. category is "Delayed," Serious, Non-Life Threatening)

Their condition is stable for the moment but requires watching by trained persons and frequent re-triage, will need hospital care (and would receive immediate priority care under "normal" circumstances).

Green/Wait (walking wounded) (Monterey County, California category is "Minor")

They will require a doctor's care in several hours or days but not immediately, may wait for a number of hours or be told to go home and come back the next day (broken bones without compound fractures, many soft tissue injuries).

White/Dismiss (walking wounded)

They have minor injuries; first aid and home care are sufficient, a doctor's care is not required. Injuries are along the lines of cuts and scrapes, or minor burns.

By color coding the bandage wraps by attaching triage tags to them or actually employing different colored caps, traumatized patients can quickly be directed for appropriate care.

The head trauma bandage cap for covering a head wound of a patient is used by affixing over a traumatized patient's head, a flexible cap with i. periphery edges, segments, and an opening sized to fit about and cover the forehead, crown, sides, and back of the head of a patient with a head trauma; the cap segments on the sides have cut outs around the ears to allow observation of the ear canal and reveal any bleeding or excretion of cerebrospinal fluid through the ear and the cap edges, ii, a sterile, or sterilizable, apertured net known as a "non-adherent wound contact layer" is affixed in some manner to the inside of the outer layer if the inside of the trauma bandage cap cannot be used for non-adherent wound contact; said layers would make up a cap with enough flexibility when applied with the straps to apply minimal pressure to the head to control bleeding without aggravating intracranial pressure, iii. exterior pouches that may or may not be affixed to the exterior of the flexible cap structured to removably receive and secure therein hot or cold packs, and iv. a detachable strap system release ably affixed to the cap periphery edges and structured to pass across a patient's chin to secure the cap with adjustable, fastening ends about the head in a manner to apply minimal pressure to control bleeding and loosened and re-attached to prevent circulation stoppage and avoid aggravating intracranial pressure.

The detachable one-piece strap system passes across the patient's chin and is then secured with corresponding hook and loop strips adjacent to the ear observation openings to hold the head trauma bandage cap against the patient's head to apply minimal pressure to stop bleeding and allow the cap to be sized properly to the patient's head.

A Chin Strap with enhanced stretch and recovery may be included. A nonwoven structure is processed to impart a mechanical micro-crepe, which provides improved patient comfort. The micro-crepe treatment also allows conformity and flexibility around the contours of the face, chin, etc. It's important to note that elastic or stretch materials are not required in this approach. The nonwoven fabric of the chin-strap contains thermoplastic fibers at 30% or greater.

When exposed to the heat and pressure of the micro-crepe compaction process, these thermoplastic fibers are heat set into a folded or creped format. Suitable thermoplastic fibers include polyesters, and polyolefins, which provide sufficient elongation when gently stretched. A 15-40% elongation factor is preferred. This micro-creped material still allows welding or gluing to the trauma bandage cap on one side while attaching to a micro-hook landing pad on the other end. This micro-hood material is related to traditional hook and loop strips, but the hooks are so small they are difficult to feel. Gripping power and the ability to release and reattach remain. Micrex Corporation, Walpole Mass., is a traditional supplier of equipment and processing for the micro-creping process. The preferred chin-strap material is a 55 gsm hydroentangled nonwoven with a 70/30 polyester/rayon blend. J. Holm and several other nonwoven suppliers manufacture this and similar products.

Where head or spinal injuries are present or suspected, the patient is immobilized first before applying the head trauma bandage cap. In addition, different colored triage tags used in conjunction with head trauma bandage caps to indicate different triage categories may be applied to indicate the severity of a patient's injuries, and are selectively applied to a patient to indicate the type of medical response required.

The method of using a head trauma bandage cap exterior pouches also may vary to accommodate removable hot or cold packs, which are selectively employed. When needed to reduce swelling cold packs are applied. To preserve body heat in non-head trauma situations hot packs are applied.

The flexible head trauma bandage cap allows the head to swell from cranial pressure, but provides sufficient contact with the wound to minimize bleeding. It is particularly suited for emergency field use, where rapid stabilization of a patient is required fur transport. Minor cuts on the head often bleed heavily because the face and scalp have many blood vessels close to the surface of the skin. This bleeding is alarming, but often the injury is not severe and the bleeding will stop with modest pressure treatment. Head wounds encountered in the field must be quickly covered to minimize bleeding to stabilize the patient for rapid transport for emergency treatment. Traditional bandaging requires multiple strips of gauze or sterile wrappings to be wound about the patient's head. This is often time consuming and often requires the head to be repeatedly lifted or moved, which can aggravate or severely compromise spinal injuries.

The Boukanov type inflatable compression bandage may aggravate open wounds by applying too much cranial pressure. The present flexible head trauma bandage cap is quickly applied over the cranium in a manner, which does not compromise cervical spine immobilization that can occur with conventional bandage wrapping. It not only controls bleeding, but it does not overly apply excessive pressure on the wound to restrict circulation or aggravate intracranial pressure.

If head swelling occurs, the flexible head trauma bandage cap's securing straps may be loosened and re-affixed to prevent increasing intracranial pressure.

It also has sufficient size, when secured, to accommodate swelling and hold the cold packs placed in pouches in place about the patent's head for closed dermal head injuries (hematomas) to control swelling. These external pouches may or may not be attached around the cap exterior into which the cold packs may be inserted to avoid contaminating the dressing liner or producing an ill-fitting wrap bandage.

The head trauma bandage cap will be contained within a sterile packaging, which would be removed just prior to use.

As the head trauma bandage cap is a single layer or layered one-piece dressing, it is designed for simple, safe and quick application to the patient's head to control bleeding while minimizing movement to the patient's head. The biggest challenge in treating a head injury with bleeding is to minimize movement of the patient's head while effectively applying a dressing, which will treat the wound and remain secure and intact on the patient's head. In any situation involving a head injury, with or without bleeding, there is also the chance of injury to the neck, back and spinal column. While treating the patient it is extremely important to minimize any action that will cause the head to move, possibly resulting in further injury to the spinal region. Protocols for the treatment of head injuries dictate caregivers to apply a cervical collar around the patient's neck and then secure the patient to a backboard in order to protect the spine. In the emergency medical field the trauma cap may be slid on and secured to the patient's head by one caregiver while a second caregiver maintains cervical spinal immobilization on the patient's head according to protocol, either before or after the patient is placed on the backboard. The proper application of the head trauma bandage cap minimizes head and neck movement, which reduces the chances of cervical-spinal compromise to the patient.

With traditional methods of treating head trauma, a separate dressing is applied to the wound followed by a wrap bandage, which is wound in such a way as to secure the dressing to the wound. This method has its drawbacks as, based on the location of the wound on the head plus other challenges such as hair thickness, possible head movement etc., it is often difficult to secure the bandage. This results in the bandage slipping off of the patient's head and the need to re-apply a new dressing. In situations involving major head trauma, this can be critical in terms of blood loss, head movement, spinal column compromise and extended on-scene time.

The head trauma bandage cap is capable of being applied in such a way to quickly, safely, and effectively cover and secure whichever part of the head needs protecting. When placed in position, it covers the top/forehead, sides, and back of the head, which are the areascausing challenges using traditional bandaging methods.

The invention is thus particularly suited for emergency treatment of accident victims with head wounds. These are quickly bandaged before patient transport, thereby reducing triage time. This allows the patient to be more rapidly transported to a hospital where the head trauma bandage cap is quickly removed for examination and the wound treated.

The head trauma bandage cap is thus readily slid onto the head of a traumatized patient in the field. It is particularly suited to be placed in a manner to not interfere with cervical spine immobilization of an immobilized patient with spinal or neck injuries. It is fast and easy to apply to not only apply gentle direct pressure to a head wound, but also to control the bleeding to enable other treatment of the patient to be completed. If bleeding is profuse and if needed, additional dressings may be inserted into the interior of the cap prior to its application to absorb and control bleeding.

The invention thus provides an emergency head bandage that doesn't compromise cervical spine immobilization and, when applied, doesn't come apart during treatment and transport, and doesn't require a caregiver to re-wrap the dressing.

DESCRIPTION OF THE DRAWINGS

FIG. 3 is a front view of the embodiment shown in FIG. 1.

FIG. 4 is a top view of the embodiment shown in FIG. 1.

FIG. 5 is a side view of the embodiment shown in FIG. 1.

FIG. 10 is a front view of the embodiment shown in FIG. 8.

FIG. 11 is a top view of the embodiment shown in FIG. 8.

FIG. 12 is a side view of the embodiment shown in FIG. 8.

DESCRIPTION OF THE ILLUSTRATED EMBODIMENTS

Figure 1:
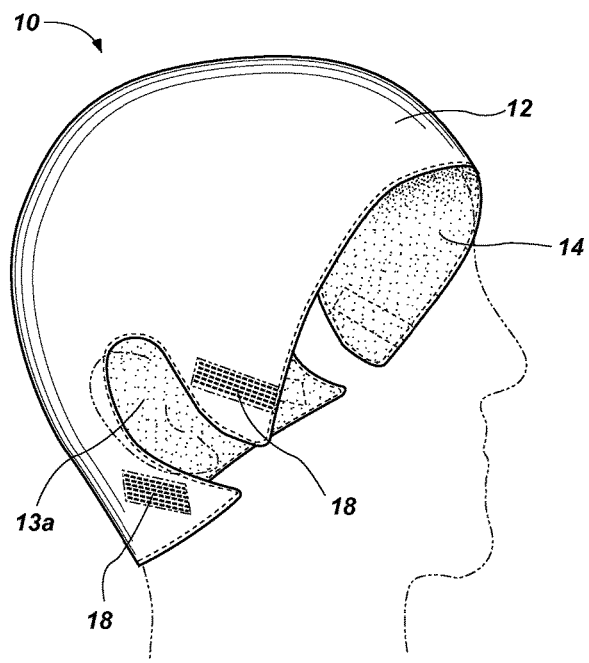
FIG. 1 is a perspective view of one embodiment of the invention.
Figure 2:
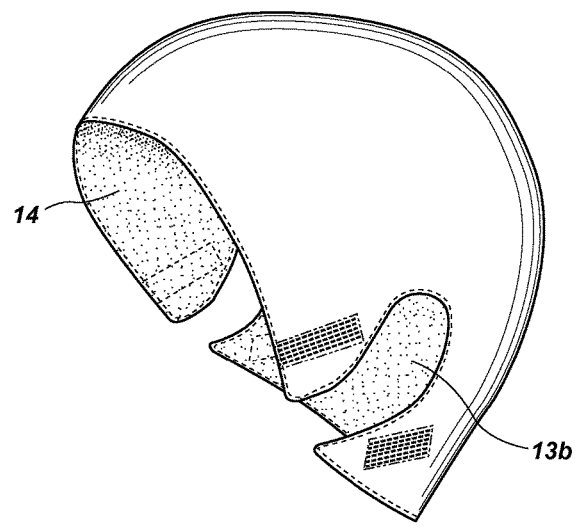
FIG. 2 is an opposite perspective view of the embodiment shown in FIG. 1.

FIG. 1 is a perspective view of an embodiment of the invention 10, shown affixed about the head of a patient. FIG. 2 is an opposite perspective view of the embodiment shown in FIG. 1. The invention 10 comprises a flexible cap 12 with enough stretch to fit about the forehead, back, sides, and upper part of a patient's head securing the cap 12 with ear observation openings 13a, 13b shown in FIGS. 1, 2 about the ears of a patient. Ear observation openings 13a, 13b expose the ears of the patient to allow emergency responders to monitor the absence or presence of cerebrospinal fluid and or blood, which may result from head trauma to the patient.

The stretchable flexible cap 12 applies gentle compression force around the head to stop bleeding, but is structured to be loosened and re-attached to prevent circulation restriction and avoid aggravating intracranial pressure.

The cap 12 has an interior sterile dressing liner 14 preferably constructed of an absorbent material, such as cotton, which may stretch approximately 20% to apply gentle pressure on a head wound. It also has sufficient give to accommodate intracranial swelling. The flexible or non-flexible cap 12 and liner 21 have enough flex when placed on a patient to apply gentle pressure to control bleeding. It is also flexible to hold cold packs 15 in place, where necessary, about the patent's head for a closed dermal head injury (hematomas).

FIG. 3 is a front view of the embodiment shown in FIG. 1.

FIG. 4 is a top view of the embodiment shown in FIG. 1.

FIG. 5 is a side view of the embodiment shown in FIG. 1.

Figure 6:
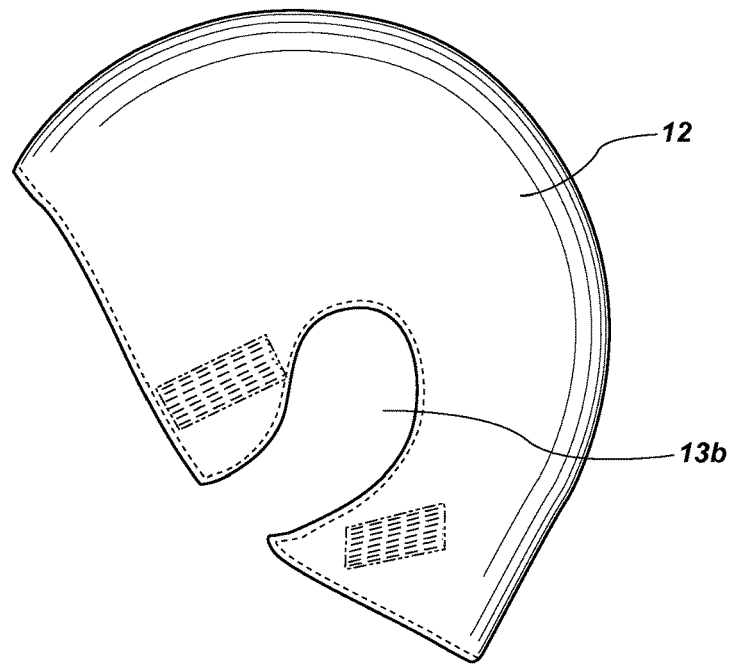
FIG. 6 is an opposite side view of the embodiment shown in FIG. 5.

FIG. 6 is an opposite side view of the embodiment shown in FIG. 5.

Figure 7:
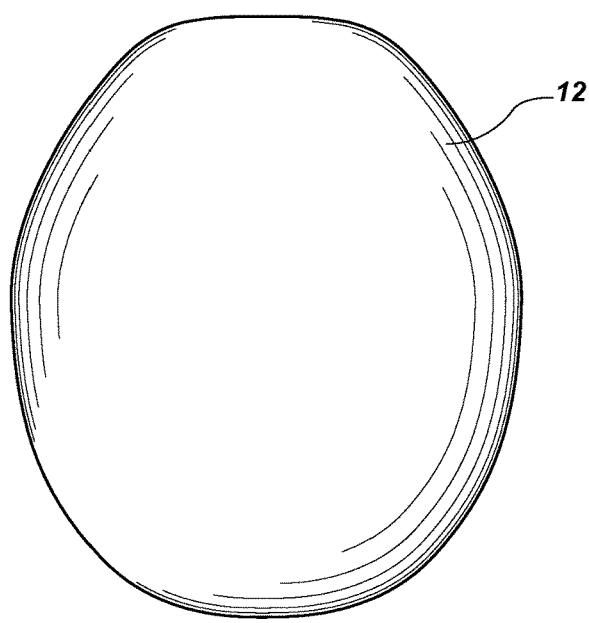
FIG. 7 is a top view of the embodiment shown in FIG. 6.

FIG. 7 is a top view of the embodiment shown in FIG. 6.

Figure 8:
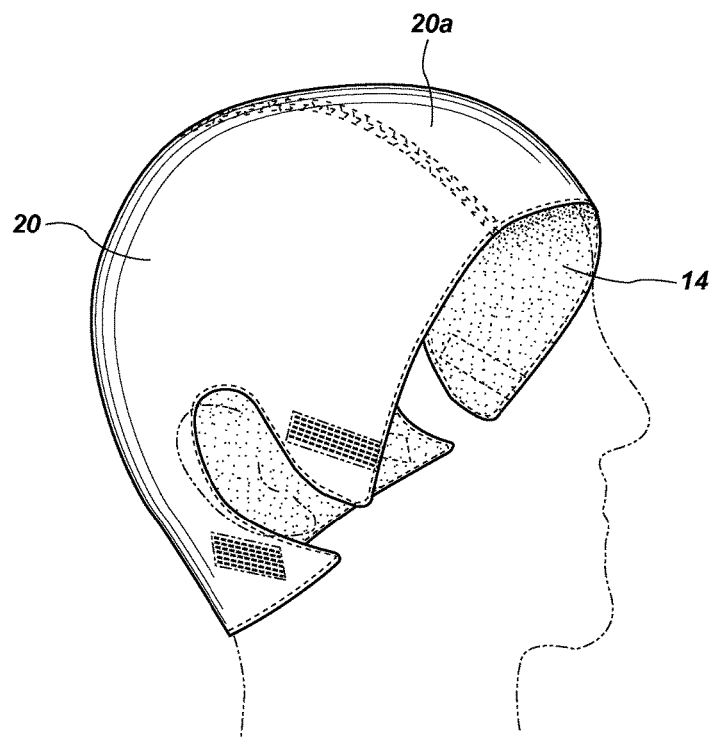
FIG. 8 is a perspective view of another embodiment of the invention.

FIG. 8 is a perspective view of another embodiment of the invention wherein the cap 12 is constructed of three panels 20, 20a, and 20b sewn or joined together. The cap 12 consists of three panels, a top 20a, and two side segments 20, 20b connected to cover the forehead/crown, sides and back of the head. Ear observation openings 13a, 13b in the side segments 20, 20b around the ears allow caregivers to observe any fluid discharge through the ears. A sterile dressing liner 14 is affixed to the inside of the cap 12. The cap 12 and liner 14 are constructed of a material with enough flex when placed on a patient to apply minimal pressure to the head to control bleeding without aggravating intracranial pressure.

Figure 9:
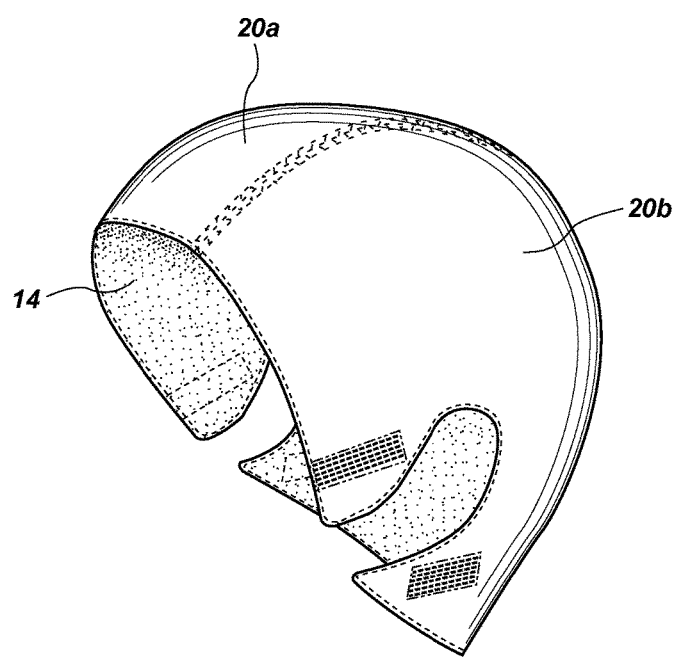
FIG. 9 is an opposite perspective view of the embodiment shown in FIG. 8.

FIG. 9 is an opposite perspective view of the embodiment shown in FIG. 8.

FIG. 10 is a front view of the embodiment shown in FIG. 8.

FIG. 11 is a top view of the embodiment shown in FIG. 8.

FIG. 12 is a side view of the embodiment shown in FIG. 8.

Figure 13:
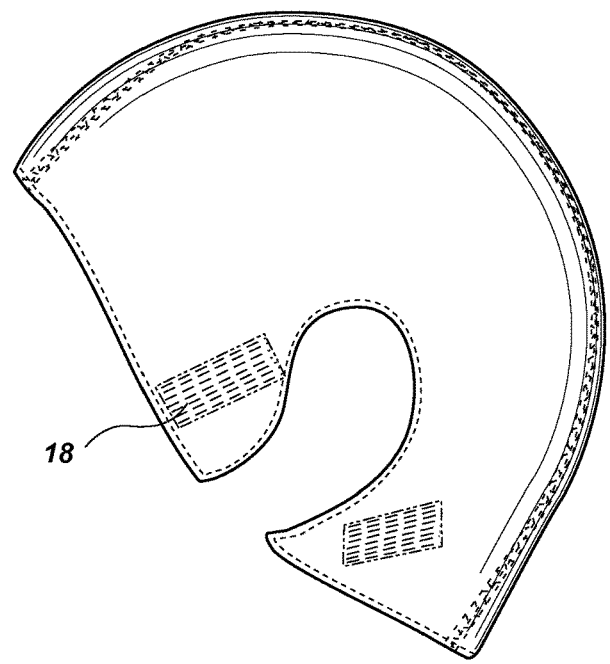
FIG. 13 is an opposite side view of the embodiment shown in FIG. 12.

FIG. 13 is an opposite side view of the embodiment shown in FIG. 12.

Figure 14:
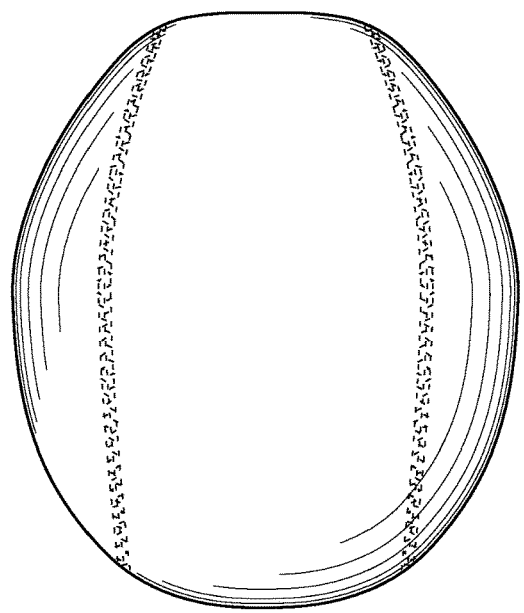
FIG. 14 is a top view of the embodiment shown in FIG. 13.

FIG. 14 is a top view of the embodiment shown in FIG. 13.

Figure 15:
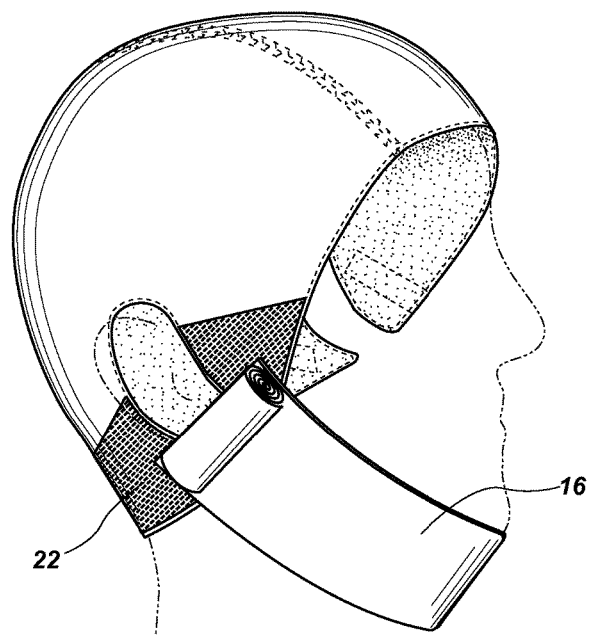
FIG. 15 is a perspective view of another embodiment of the invention.
Figure 16:
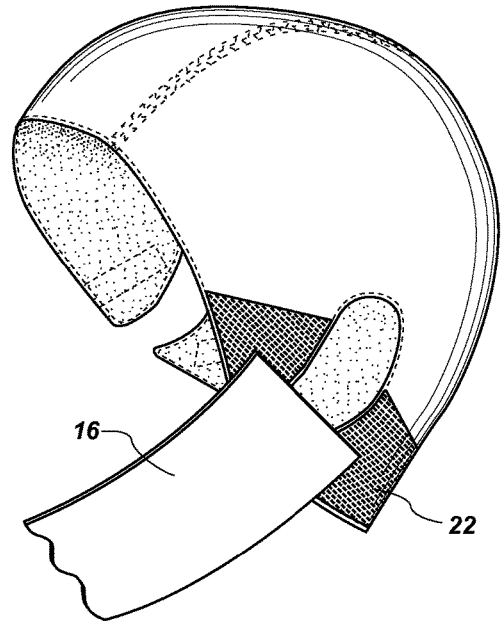
FIG. 16 is an opposite perspective view of the embodiment shown in FIG. 15.

FIG. 15 is a perspective view of another embodiment of the invention. FIG. 16 is an opposite perspective view of the embodiment shown in FIG. 15. To secure the cap 12 in place, an adjustable strap 16 is included to affix removably to the peripheral edges of the sides of the cap 12. To removably secure the adjustable strap 16 to the cap 12, micro-hook areas 22 are affixed to the peripheral edges of the sides of the cap 12 as shown in FIGS. 15 and 16. Corresponding hook and loop strips (not shown) are then attached to the ends of the adjustable strap 16, or the adjustable strap is made of a corresponding micro-hook material to removably secure it to the peripheral edges of the sides of the cap 12 as shown in FIGS. 15 and 16.

FIGS. 15 and 16 illustrate the simplest embodiment of an adjustable strap 16, which comprises a rolled-up wide band made of a micro-hook material, which is attached to the corresponding micro-hook areas 22 of the edges of the cap 12 positioned so that when the strap 16 is attached, it does not cover the ear observation openings 13a, 13b as shown in FIGS. 15 and 16. The strap 16 is initially stored in a rolled-up position and secured to the micro-hook areas 22. The cap 12 is positioned on the head of a patient, and the strap 16 unrolled and secured in position to the micro-hook areas 22.

Figure 17:
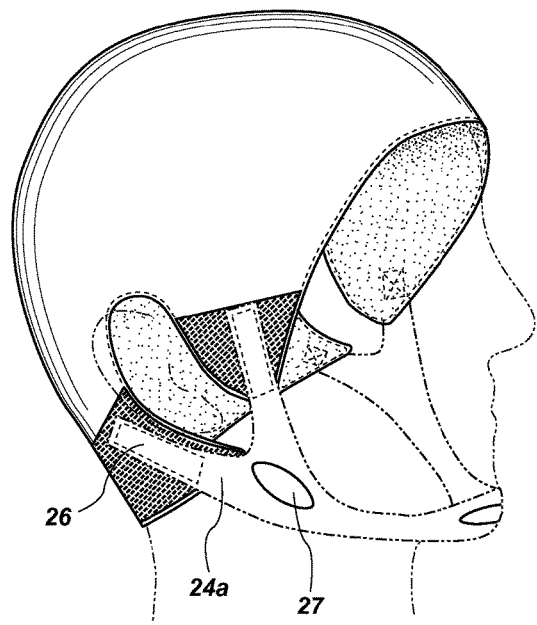
FIG. 17 is a perspective view of the embodiment shown in FIG. 15 with a different chin strap system.
Figure 18:
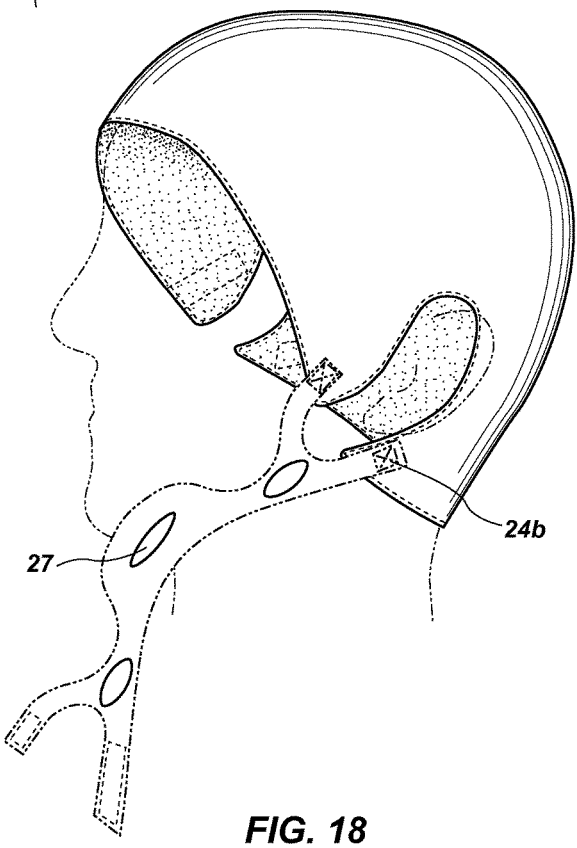
FIG. 18 is an opposite perspective view of the embodiment shown in FIG. 17.

FIG. 17 is a perspective view of the embodiment shown in FIG. 15 with a different chin strap system. FIG. 18 is an opposite perspective view of the embodiment shown in FIG. 17.

FIGS. 17 and 18 employ a different chin strap system with Y shaped ends 24a, 24b. The 24a ends include hook and loop strips 26 which removably secure to the micro-hook areas 22 for strap adjustment. The other 24b ends are affixed to the bottom of one of the peripheral edges of the sides of the cap 12 as shown in FIG. 18.

The Y shaped adjustable strap 16 includes three holes 27 to better conform to the face when strapped to allow additional gentle pressure to be applied by adjusting the hook and loop strips 26 to the micro-hook areas 22 to hold the cap 12 anchored from under the chin about the head to control bleeding.

Figure 19:
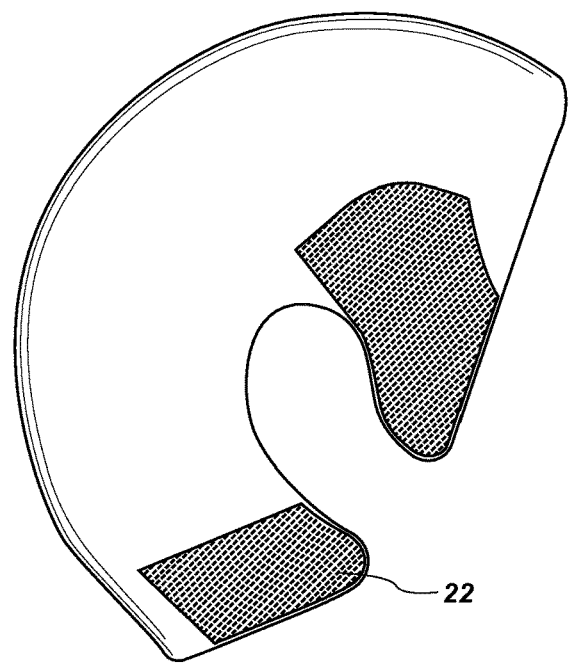
FIG. 19 is a perspective view of a variation of the embodiment of FIG. 17.
Figure 20:
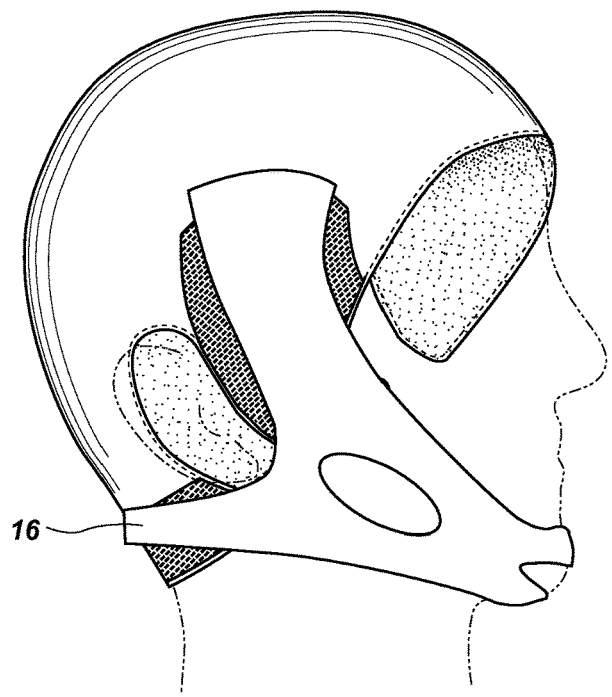
FIG. 20 is perspective view of the embodiment shown in FIG. 17 with a wider chin strap system.

FIG. 19 is a perspective view of a variation of the embodiment of FIG. 17 showing larger micro-hook areas 22 to accommodate a wider Y shaped chin strap system 16 shown in FIG. 20.

Figure 21:
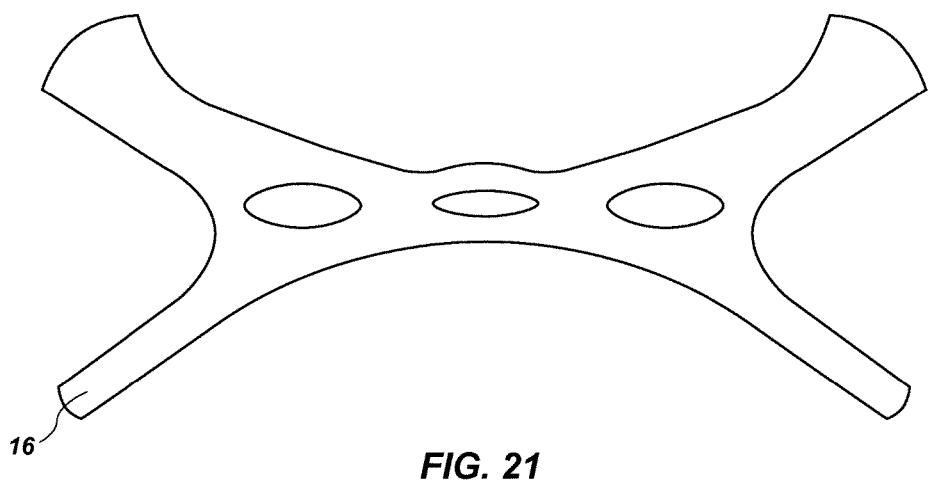
FIG. 21 is a top view of the chin strap system embodiment of FIG. 20.

FIG. 21 is a top view of the chin strap system 16 embodiment of FIG. 20.

Figure 22:
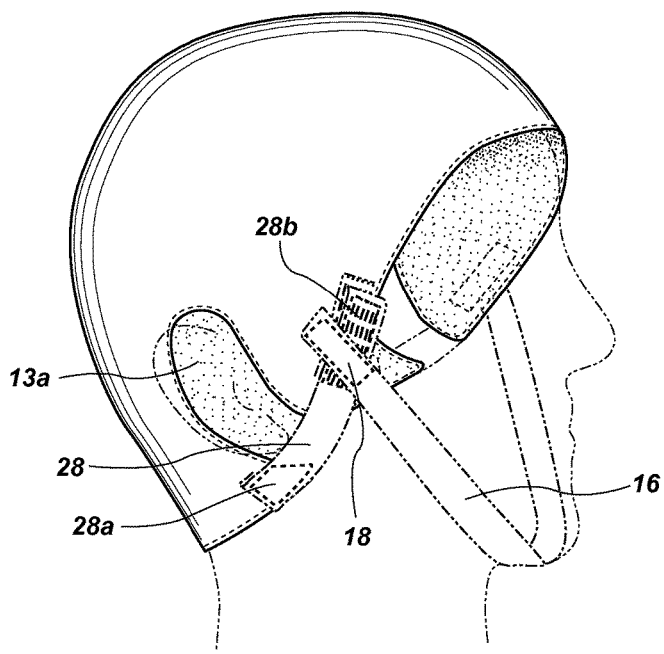
FIG. 22 is a perspective view of another embodiment of the invention.

FIG. 22 is a perspective view of another embodiment of the invention. Further cap adjustments are made with adjustable straps 28 shown in FIG. 22 which adjust the size of the ear observation openings 13a, 13b. One end 28a of adjustable straps 28 is affixed to the peripheral edge of the cap 12 proximate the base of the ear hole 13a. The other end 28b has hook and loop strips (not shown) adapted to attach to corresponding hook and look strip proximate the opposite base of the ear hole 13a to adjust and help fit and secure cap 12 about the ears. In this embodiment the adjustable chin strap 18 is thus secured after looping under the patient's chin.

Figure 23:
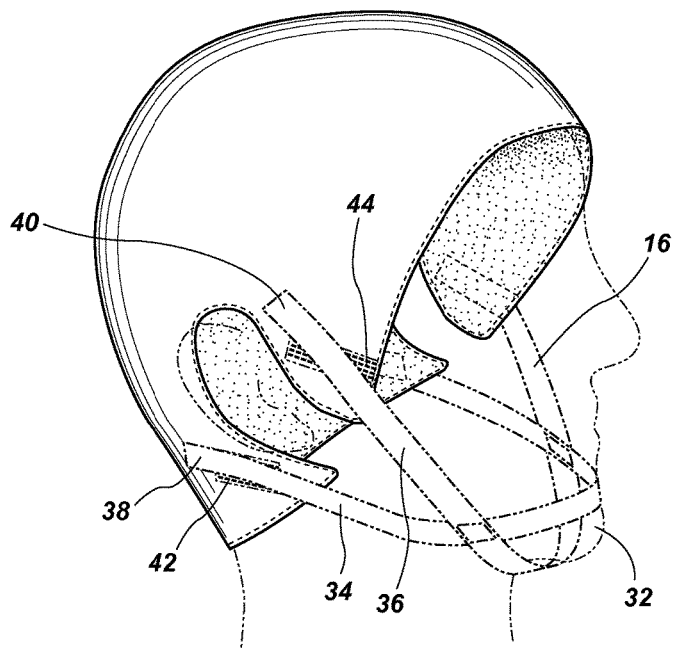
FIG. 23 is a perspective view of the embodiment shown in FIG. 22 with a different chin strap system.

FIG. 23 is a perspective view of the cap embodiment shown in FIG. 22 with a different detachable chin strap system 16 with a chin cup 32 formed by two crossing straps 34, 36 with ends 38, 40 secured with hook and loop strips 42, 44 affixed to the cap 12 periphery edges. The detachable strap system 16 was structured to secure the chin cup 32 about a patient's chin to removably secure the cap 12 to the head in a manner to apply minimal pressure to control bleeding without aggravating intracranial pressure in one mode, and be loosened and re-attached in another mode to prevent circulation restriction and avoid aggravating intracranial pressure.

Figure 24:
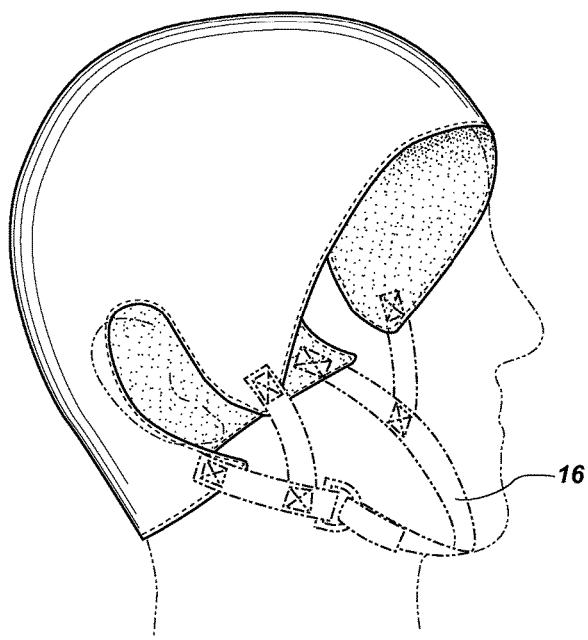
FIG. 24 is a perspective view of another embodiment of the invention.

FIG. 24 is a perspective view of another embodiment of the invention employing a D-ring chin strap 16 system to secure the cap 12 to the head of a patient.

Figure 25:
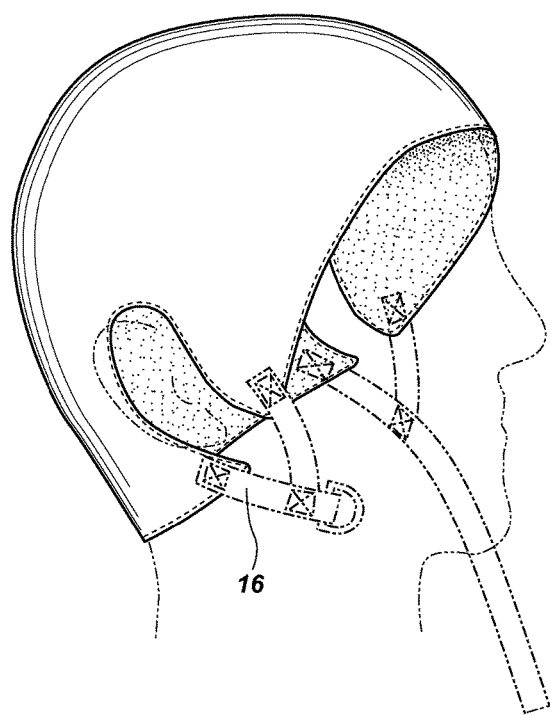
FIG. 25 is a perspective view of the embodiment of the invention shown in FIG. 24 with the chin strap system open.

FIG. 25 is a perspective view of the embodiment of the invention shown in FIG. 24 with the chin strap 16 system open.

Figure 26:
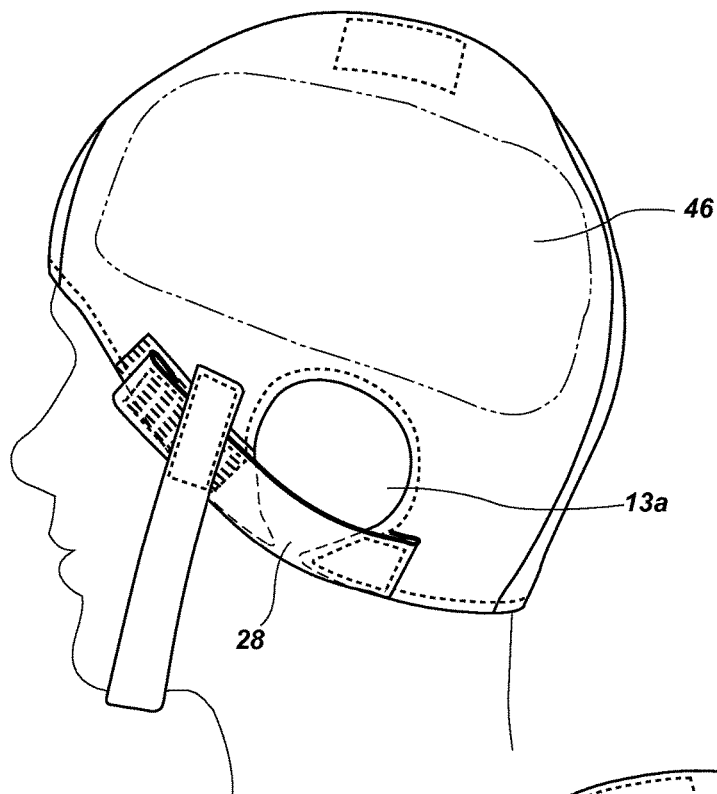
FIG. 26 is a side view of another embodiment of the invention.

FIG. 26 is a side view of another embodiment employing a super absorbent fiber (SAF) layer 46 instead of cold packs and pouches. The SAF layer 46 is integrated within the cap 12 in lieu of the sterile dressing liner 14 and may be shaped as a discrete part or panel or shaped in selected areas only placed to absorb most fluids from head wounds. Alternatively, the SAF layer 46 may be added as an additional layer covering the entire interior of the cap 12.

Figure 27:
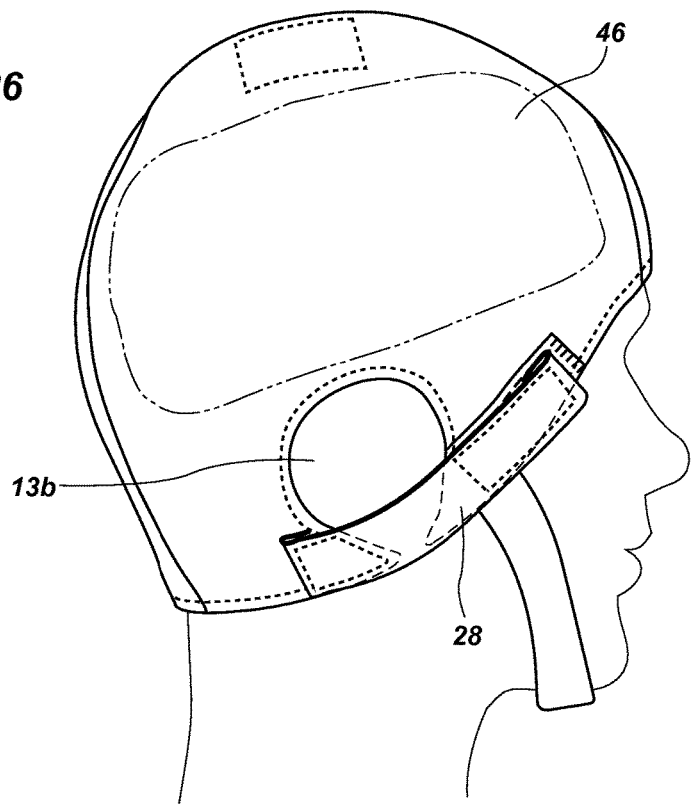
FIG. 27 is the opposite side view of the embodiment shown in FIG. 26.

FIG. 27 is the opposite side view of the embodiment shown in FIG. 26.

Figure 28:
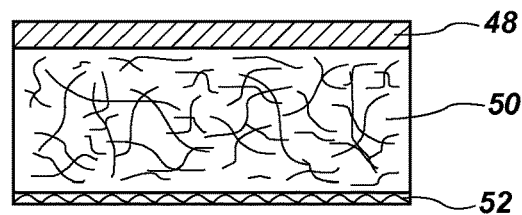
FIG. 28 is a cross section view of one embodiment of a three layer cap material.

FIG. 28 is a cross section view of one embodiment of a three layer cap material. An exterior laminated film 48 covers a non-woven SAF layer 50 affixed to a perforated non-absorbent wound contact interior layer 52.

Figure 29:
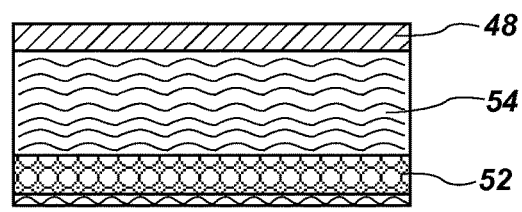
FIG. 29 is a cross section view of another embodiment of a three layer cap material.

FIG. 29 is a cross section view of another embodiment of a three layer cap material having an exterior laminated film 48 covering a nonwoven SAF dry layer 54 affixed to a perforated non-absorbent wound contact interior layer 52.

Figure 30:
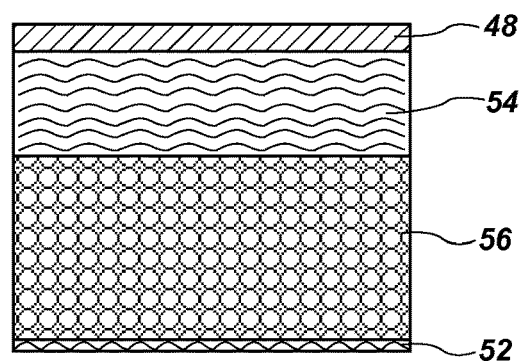
FIG. 30 is a cross section view of another embodiment of a four layer cap material

FIG. 30 is a cross section view of another embodiment of a four layer cap material having an exterior laminated film 48 covering a nonwoven SAF dry layer 54, which covers an SAF hydrated entrapped gel layer 56 secured by a perforated non-absorbent wound contact interior layer 52.

The invention 10 is readily slid onto the head of a traumatized patient in the field while maintaining cervical spine immobilization as shown. As the invention 10 is of one-piece construction, it will not come apart during treatment or transport. It is fast and easy to apply to not only apply gentle pressure to the head wound, but also to control the bleeding to enable other treatments of the patient to be completed. If bleeding is profuse and if needed, additional dressings may be inserted into the interior of the cap prior to its application to control bleeding.

The above description and specification should not be construed as limiting the scope of the claims but as merely providing illustrations of some of the presently preferred embodiments of this invention. Thus, the claims themselves contain those features deemed essential to the invention.

We claim:

1. A head trauma bandage cap comprising:
    a. a flexible cap made of
        i. an exterior flexible weather resistant or waterproof material with periphery edges, top and sides defining ear observation openings cut out and adapted to be positioned proximate a patient's ears to enable caregivers to observe any fluid discharge from the patient's ears and variably secured together with a strapping system in a manner so that the ear observation openings may be varied in size as the strapping system is varied in position, and an opening sized to fit about and cover a forehead/crown, sides, and back of the patient's head; and
        ii. an interior made of absorbent materials that has a non-adherent wound contact surface, with enough flex when placed on the patient to apply minimal pressure to the patient's head to control bleeding without aggravating intracranial pressure and can be hydrated and chilled or frozen to provide an extended duration cooling device; and
    b. a stretch and recovery chin strap part of the strapping system allows conformity and flexibility around contours of the face with releasable fasteners affixed to the periphery edges of the flexible cap and structured to secure the chin strap about the patient's chin to removably secure the flexible cap to the patient's head in a manner to apply minimal pressure to control bleeding without aggravating intracranial pressure in one mode, and loosened and re-attached in another mode to prevent circulation restriction and avoid aggravating intracranial pressure.

2. A head trauma bandage cap according to claim 1, wherein the exterior flexible weather resistant or waterproof material is laminated with layers of film and reinforcing and/or cushioning materials using a permanently flexible adhesive, and/or stitching, which together form a flexible composite structure providing a barrier with stretch and recovery properties to help prevent penetration of bacteria, pathogens or contaminants.

3. A head trauma bandage cap according to claim 2, wherein the exterior flexible weather resistant or waterproof material is a monolithic barrier and the interior has an hydrophobic chemical treatment, which allows air permeability but resists fluid penetration.

4. A head trauma bandage cap according to claim 3, wherein the interior has an hydrophobic chemical treatment, which when placed over the skin, allows moisture or perspiration from skin to escape.

5. A head trauma bandage cap according to claim 2, wherein the interior is made of a flexible fibrous absorbent or superabsorbent polymer (SAP or SAF) component of a soft textile or nonwoven material that can absorb fluids.

6. A head trauma bandage cap according to claim 5, wherein the interior can be hydrated, chilled or frozen to provide an extended duration cooling article.

7. A head trauma bandage cap according to claim 1, including antimicrobials placed in the interior in an additional interior absorbent layer, or on the exterior flexible weather resistant or waterproof material to reduce bacterial populations and infections.

8. A head trauma bandage cap according to claim 7, wherein the antimicrobials are selected from the group comprising traditional silver-ion releasing antimicrobials, quaternary amines and oxidizers, iodine, chlorine or chlorhexidine gluconate (CHG).

9. A head trauma bandage cap according to claim 7, wherein the antimicrobials are 200 ppm of elemental silver embedded in a polyurethane polymer blend.

10. A head trauma bandage cap according to claim 1, wherein the exterior flexible weather resistant or waterproof material comprises a monolithic-breathable film and the interior has an hydrophobic chemical treatment with no holes or direct passages that acts as a bacteria and viral barrier.

11. A head trauma bandage cap according to claim 1, wherein the exterior flexible weather resistant or waterproof material is constructed of polyurethanes, polyolefins, block-copolymers, polyamides, or blends forming a barrier-dressing so exterior particles, fluids and pathogens cannot penetrate from outside toward the patient.

12. A head trauma bandage cap according to claim 1, wherein the releasable fasteners comprise corresponding hook and loop technology.

13. A head trauma bandage cap according to claim 1, wherein the flexible cap is color-coded to indicate severity of the patient's injuries in an emergency trauma triage setting.

14. A head trauma bandage cap according to claim 1, wherein ends of the chin strap are Y shaped, and including a hole in the chin strap adapted to be proximate the chin to conform to the contours of the face.

15. A method of making a head trauma bandage cap for covering a patient with a head wound comprising:
    a. constructing a flexible cap with
        i. an exterior made of a flexible weather resistant or waterproof material with periphery edges, top and sides defining ear observation openings cut out and adapted to be positioned proximate the patient's ears to enable caregivers to observe any fluid discharge from the patient's ears and variably secured together with a strapping system in a manner so that the ear observation openings may be varied in size as the strapping system is varied in position, and an opening sized to fit about and cover a forehead/crown, sides, and back of a head of the patient, and ii. an interior made of a sterile absorbent or superabsorbent polymer non-adherent wound contact surface, with enough flex when placed on the patient to apply minimal pressure to the patient's head to control bleeding without aggravating intracranial pressure and can be hydrated and chilled or frozen to provide an extended duration cooling device; and b. affixing a chin strap that is a part of the strapping system with a nonwoven structure processed to form a stretch and recovery or mechanical micro-crepe allowing conformity, elasticity and flexibility around contours of the face with releasable fasteners affixed to the periphery edges of the flexible cap and structured to secure the chin strap about the patient's chin to removably secure the flexible cap to the patient's head in a manner to apply minimal pressure to control bleeding without aggravating intracranial pressure in one mode, and loosened and re-attached in another mode to prevent circulation restriction and avoid aggravating intracranial pressure.

16. A method of making a head trauma bandage cap according to claim 15, wherein the exterior flexible weather resistant or waterproof material is laminated with layers of film and reinforcing and/or cushioning materials forming a flexible adhesive, which together form a flexible composite structure providing a monolithic barrier film to help prevent penetration of bacteria, pathogens or contaminants.

17. A method of making a head trauma bandage cap according to claim 16, including antimicrobials placed in a sterile non-adherent wound-contact surface, an absorbent layer, or in a waterproof-breathable outer layer to reduce bacterial populations and infections.

18. A method of making head a trauma bandage cap according to claim 17, wherein the antimicrobials are 200 ppm of elemental silver embedded in a polyurethane polymer blend.

19. A method of making a head trauma bandage cap according to claim 18, wherein the releasable fasteners comprise corresponding hook and loop strips.

20. A method of making a head trauma bandage cap according to claim 17, wherein the antimicrobials are selected from the group comprising traditional silver-ion releasing antimicrobials, quaternary amines and oxidizers, iodine, chlorine or chlorhexidine gluconate (CHG).

21. A method of making a head trauma bandage cap according to claim 16, wherein the exterior flexible weather resistant or waterproof material comprises a monolithic barrier, which allows air permeability but resists fluid penetration allowing moisture or perspiration from skin to escape.

22. A method of making a head trauma bandage cap according to claim 16, wherein the exterior flexible weather resistant or waterproof material comprises a monolithic barrier film with no holes or direct passages that acts as a bacteria and viral barrier.

23. A method of making a head trauma bandage cap according to claim 16, wherein the exterior flexible weather resistant or waterproof material is constructed of polyurethanes, polyolefins, block-copolymers, polyamides, or blends forming a barrier-dressing so exterior particles, fluids and pathogens cannot penetrate toward the patient.

24. A method of making a head trauma bandage cap according to claim 15, wherein the interior is formed of a flexible fibrous nonwoven absorbent or superabsorbent polymer (SAP or SAF) soft textile or nonwoven material that can absorb fluids.

25. A method of making a head trauma bandage cap according to claim 24, wherein the flexible fibrous nonwoven absorbent or superabsorbent polymer (SAP or SAF) interior can be hydrated, chilled or frozen to provide an extended duration cooling article.

26. A method of making a head trauma bandage cap according to claim 15, including marking the flexible cap with different triage color codes to indicate severity of the patient's injuries in an emergency trauma triage setting.

* * * * *